United States Patent [19]
McGann

[11] Patent Number: 5,199,869
[45] Date of Patent: Apr. 6, 1993

[54] ORTHODONTIC SPRING

[76] Inventor: Don McGann, 15 No. Vista de Catalina, South Laguna, Calif. 92677

[21] Appl. No.: 506,711

[22] Filed: Apr. 9, 1990

[51] Int. Cl.$^5$ ................................................ A61C 3/00
[52] U.S. Cl. ......................................... 433/21; 433/149
[58] Field of Search .................................. 433/21, 149

[56] References Cited

U.S. PATENT DOCUMENTS

| | | | |
|---|---|---|---|
| 2,897,598 | 8/1959 | Kesling | 433/149 |
| 3,052,029 | 9/1962 | Wallshein | 433/21 |
| 3,664,023 | 5/1972 | Pool | 433/21 |
| 3,837,082 | 9/1974 | Pool | 433/149 |
| 4,256,456 | 3/1981 | Wallshein | 433/21 |

Primary Examiner—John J. Wilson

[57] ABSTRACT

An appliance for separating a pair of adjacent teeth comprising a wire spring formed into an approximate U-shape having two leg segments and a connecting bridge segment. The leg segments are drawn to either side of a reference plane such that the bridge segment is in torsional strain when the leg segments are near coplanar. This torsional strain causes the legs to apply a force to the proximal walls of the adjacent teeth. One leg has a hook end which acts an an anchor in the lingual or the buccal embrasure during installation of the spring, while the other leg has an abrupt bend which acts as an antirotational feature.

2 Claims, 2 Drawing Sheets

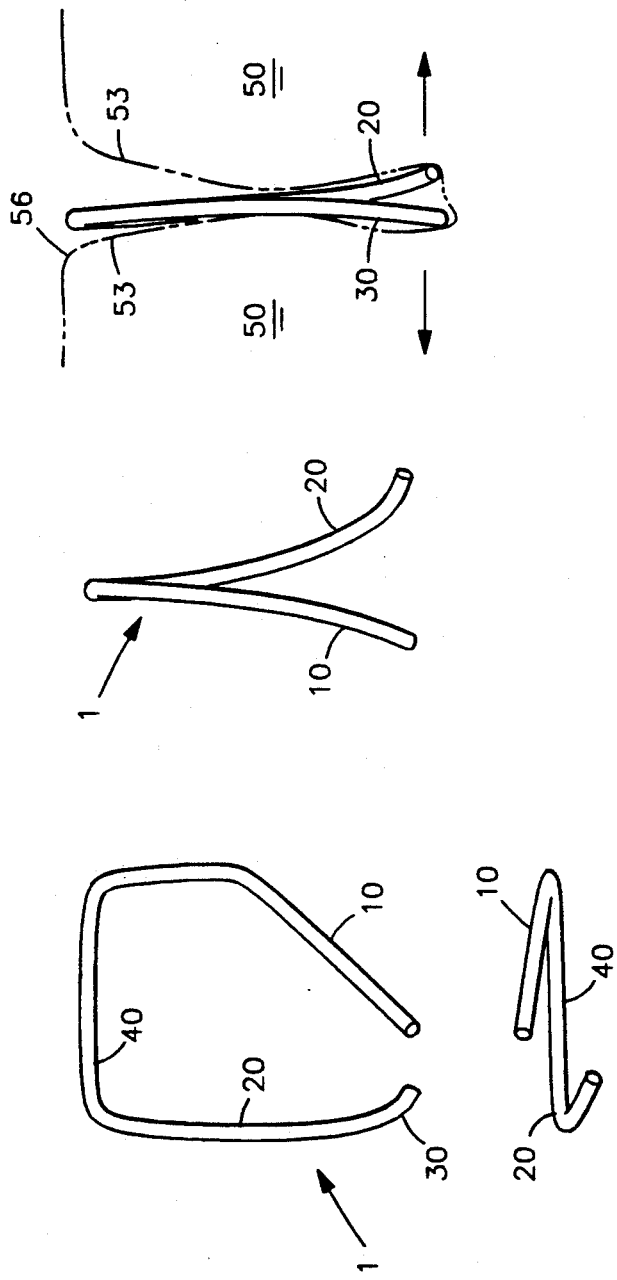

ORTHODONTIC SPRING

BACKGROUND OF THE INVENTION AND DESCRIPTION OF THE PRIOR ART

The invention relates to the field of orthodontic springs used for the movement of teeth in dentistry. The prior art teaches several alternate spring devices for separating, rotating and righting teeth which require orthodontic attention. Among the prior art springs is a double loop spring having a pair of legs which move toward each other within the plane of the tooth interface, thereby applying a separating force to the teeth by wedging itself between the teeth on opposite sides. In another form, the spring's legs are initially forcefully wedged between and thereby separate adjacent teeth. One example of the latter device has double legs which are forced into an overlap position upon installation thereby generating a lateral spreading force to adjacent teeth. This approach has the disadvantage of providing the largest force at the moment of installation but which thereafter rapidly diminishing.

Patents: U.S. Pat. Nos. 2,897,598, 3,052,029, 3,664,023, 3,827,082, and 4,256,456, fully describe the prior art. These prior springs are generally bulky, providing discomfort to the wearer as they are made of relatively heavy gauge wire and sheet materials which protrude beyond the tooth line thereby interfering with normal speaking and eating function. Some of these devices are designed to penetrate the gum ridge or are forcefully wedged between teeth thereby causing pain and in some cases, extreme discomfort. The orthodontics field is only now starting to realize that the prior art springs have spring rates several times larger than is required for successfully moving teeth in the practice. Also, prior art springs often have complex shapes requiring expensive tooling and added labor for fabrication. To summarize, the prior art teaches orthodontic springs which are bulky, have complex shapes, are uncomfortable and painful to wear, which are difficult to install and which often rotate or fall out of place after a short time. The material most often used in prior art springs is a stainless steel which has high stiffness and low elastic limit and therefore is often permanently deformed during insertion thereby reducing its effectiveness. This material cannot apply a uniform force over the range of tooth separation desired so that more frequent application is required.

Therefore, there exists a need for an inexpensive orthodontic spring for applying a relatively small but continuous force, over the range of desired separation of adjacent teeth to enable movement with little discomfort to the wearer. The present invention fulfills these needs in a relatively inexpensive fashion and provides further related advantages as described and shown herein.

SUMMARY OF THE INVENTION

The invention is a dental appliance used for separating a pair of adjacent teeth, and comprises a wire spring formed into an approximate U-shape having a first and a second leg segment joined by a bridge segment. The first leg segment is abruptly bent toward the second leg segment providing a non-rotating feature. The end of the second leg segment is bent into a hook shape providing an anchor means for facilitating installation and helping to prevent rotation or other undersirable movements during wear. The leg segments are bent laterally away from each other so that upon installation, when the legs are pressed together between adjacent teeth, the bridge segment undergoes torsional strain within the elastic limit.

Thus the invention provides an appliance for separating teeth which is easily installed, will not rotate or otherwise move out of place while being worn, has a low profile so as not to interfere with speaking or eating function, and applies a gentle but constant force to the adjacent teeth over the entire range of tooth motion. The invention does not generate any pain or discomfort to the wearer. The deviation of the legs provide a self-seating action keeping the bridge segment which lies on the occlusal surface out of interference with opposing teeth. Other features and advantages of the present invention will become apparent from the following, more detailed description, taken in conjunction with the accompanying drawings, which illustrate, by way of example, the principles of the invention.

DESCRIPTION OF THE DRAWINGS

FIG. 1 is a front and top view of the invention showing the general shape of the wire spring before installation;

FIG. 2 is a side view of the invention before installation which shows the extent of leg opposition;

FIG. 3 is a side view of the invention after installation showing the compressed legs and position of the invention between adjacent teeth;

FIG. 4 is a perspective view of the invention shown installed between two adjacent teeth and illustrating with arrows the direction of force exerted by the two legs upon the opposing teeth;

DETAILED DESCRIPTION OF THE PREFERRED EMBODIMENT

Figure 5:
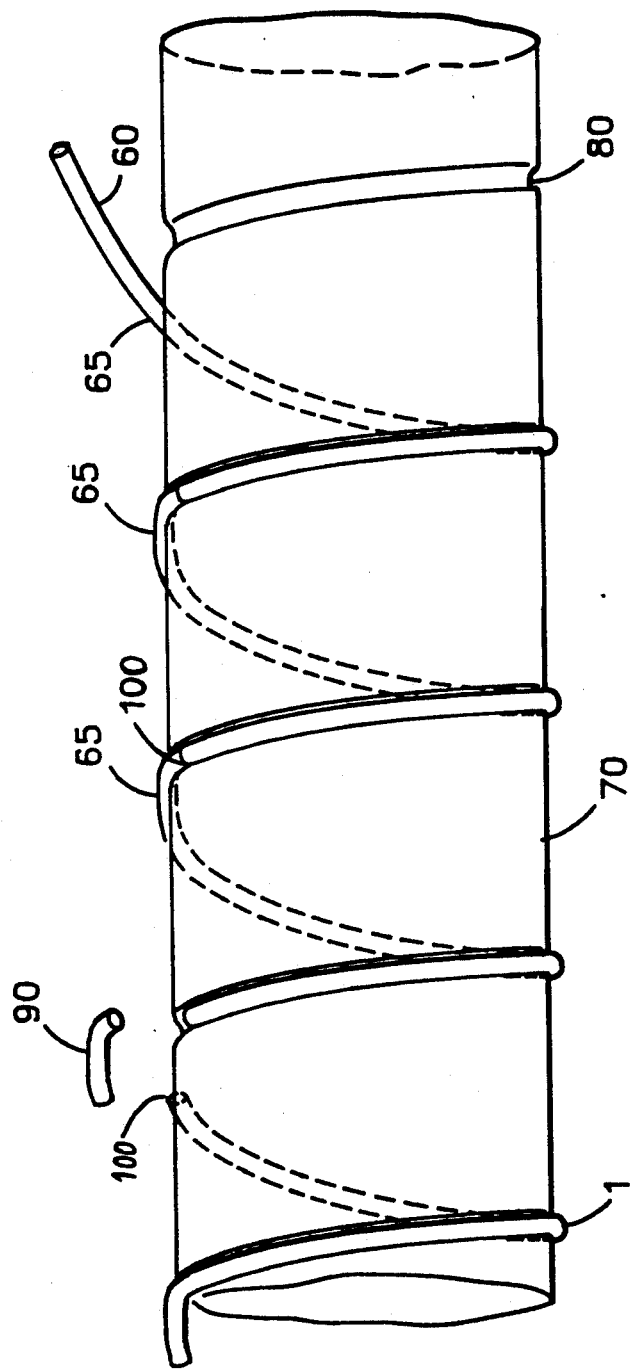

With reference to FIGS. 1-4, a wire spring 1 appliance is mounted between a pair of adjacent teeth 50 for separating the same. The spring 1 comprises a first leg segment 10 in a vertical lingual plane, a second leg segment 20 in a vertical buccal plane and a mainly straight bridge segment 40 in an occlusal plane. The bridge segment 40 joins the first and the second leg segments 10, 20 such that the bridge segment 40 is placed under a torsional load when the first and the second leg segments 10, 20 are drawn near to a common reference plane 5 such that the first leg segment 10 is seated against the proximal wall 53 of one of the adjacent teeth 50 and the second leg segment 20 is seated against the proximal wall 53 of the other of the adjacent teeth 50, whereby the torsional load causes the legs 10, 20 to apply a separating force, (shown with a letter "F"), to each of the adjacent teeth 50.

Each segment 10, 20 and 40 is approximately 3.5 to 4 mm long. First leg segment 10 has bend 11 so that first leg segment 10 is directed toward second leg segment 20. Second leg segment 20 terminates into hook shape 30. Extensions of the center lines of the ends of leg segments 10 and 20 cross with an included angle (alpha) of between 50 and 80 degrees. First and second leg segments 10, 20, as shown in FIG. 2, are bent in mutually opposite directions away from reference plane 5 and have a maximal separation at their ends of approximately 3 mm.

In use, as shown in FIGS. 3 and 4, spring 1 is placed between adjacent teeth 50, leg segments 10, 20 being forced toward each other into a compressed shape and held therein by adjacent teeth 50. Bridge segment 40, laying along occlusal plane crown line 56 is thereby placed in torsional strain producing separating forces "F" against proximal walls 53. The force generated is about 430 gm per mm of spring deflection as compared to the typical 1225 gm per mm of spring deflection of a typical stainless steel spring. Leg segments 10, 20 provide labial-lingual pinching action enhance separation and provide self seating of spring 1.

I claim:

1. A wire spring appliance for mounting between a pair of adjacent teeth for separating the same, comprising a first leg segment in a vertical lingual plane, a second leg segment in a vertical buccal plane and a mainly straight bridge segment in an occlusal plane, the bridge segment joining the first and the second leg segments such that the bridge segment is placed under a torsional load when the first and the second leg segments are drawn near to a common reference plane such that the first leg segment is seated against the proximal wall of one of the adjacent teeth and the second leg segment is seated against the proximal wall of the other of the adjacent teeth, whereby the torsional load causes the legs to apply a separating force to each of the adjacent teeth, the legs being curved in mutually divergent arcs away from the reference plane such that the separating force applied to each of the proximal walls causes the spring to move in the gingival direction, whereby the spring is self-seating and self-tightening between the adjacent teeth.

2. The spring of claim 1 wherein the first leg segment has an abrupt bend of between 20 and 60 degrees, said bend directing a major portion of the first leg segment in a direction convergent on the second leg segment such that the major portion interacts with the embrasure of the adjacent teeth to prevent rotation of the wire spring appliance.

* * * * *